United States Patent
Liu et al.

(10) Patent No.: US 12,070,309 B2
(45) Date of Patent: Aug. 27, 2024

(54) METHOD, COMPUTER PROGRAMMING PRODUCT AND ELECTRONIC DEVICE FOR CALCULATING BLOOD OXYGEN SATURATION

(71) Applicant: Wistron Corp., New Taipei (TW)

(72) Inventors: Zheng-De Liu, New Taipei (TW); You-Jyun Syu, New Taipei (TW); Ching-An Cho, New Taipei (TW); Hao-Gong Chou, New Taipei (TW)

(73) Assignee: Wistron Corp., New Taipei (TW)

( * ) Notice: Subject to any disclaimer, the term of this patent is extended or adjusted under 35 U.S.C. 154(b) by 0 days.

(21) Appl. No.: 17/319,982

(22) Filed: May 13, 2021

(65) Prior Publication Data

US 2022/0233112 A1   Jul. 28, 2022

(30) Foreign Application Priority Data

Jan. 27, 2021   (TW) ................ 110102936

(51) Int. Cl.
*A61B 5/145*   (2006.01)
*A61B 5/00*   (2006.01)

(52) U.S. Cl.
CPC ........ *A61B 5/14542* (2013.01); *A61B 5/7225* (2013.01)

(58) Field of Classification Search
CPC ... A61B 5/7225; A61B 5/7203; A61B 5/7221; A61B 5/02416; A61B 5/725; A61B 5/14552; A61B 5/145
See application file for complete search history.

(56) References Cited

U.S. PATENT DOCUMENTS

| | | | |
|---|---|---|---|
| 6,035,223 A * | 3/2000 | Baker, Jr. | A61B 5/0059 600/323 |
| 10,568,525 B1 | 2/2020 | Wu et al. | |
| 2014/0142403 A1* | 5/2014 | Brumback | A61B 5/14532 600/479 |
| 2014/0316287 A1* | 10/2014 | Watson | A61B 5/7275 600/526 |
| 2016/0066863 A1* | 3/2016 | Thaveeprungsriporn | A61B 5/7278 600/323 |
| 2018/0110429 A1 | 4/2018 | He et al. | |
| 2019/0000399 A1* | 1/2019 | Quinn | A61B 5/02125 |
| 2020/0229767 A1 | 7/2020 | Eletr et al. | |
| 2021/0338118 A1* | 11/2021 | Edouard | A61B 5/7225 |
| 2022/0280048 A1* | 9/2022 | Wu | A61B 5/742 |

FOREIGN PATENT DOCUMENTS

| | | |
|---|---|---|
| TW | 418081 B | 1/2001 |
| TW | M577569 U | 5/2019 |
| WO | WO 2013/141419 A1 | 9/2013 |

* cited by examiner

*Primary Examiner* — Eric F Winakur
*Assistant Examiner* — Abid A Mustansir

(57) ABSTRACT

A method for calculating blood oxygen saturation includes defining the extreme value point of a non-red light signal as the extreme value point of a red light signal, and calculating the blood oxygen saturation according to the extreme value point of the red light signal. The method for calculating blood oxygen saturation of the present disclosure proposes to use other light source signals to assist in finding the period of the red light signal, so that the calculation result of the red light signal is more accurate.

12 Claims, 6 Drawing Sheets

METHOD, COMPUTER PROGRAMMING PRODUCT AND ELECTRONIC DEVICE FOR CALCULATING BLOOD OXYGEN SATURATION

CROSS REFERENCE TO RELATED APPLICATIONS

This application claims priority to and the benefit of Taiwan Application No. 110102936, filed on Jan. 27, 2021, the entirety of which is incorporated by reference herein.

FIELD OF THE DISCLOSURE

The disclosure is related to a signal processing method, and in particular it is related to a method, a computer programming product, and an electronic device for calculating blood oxygen saturation.

DESCRIPTION OF THE RELATED ART

Ear-hook oximeters are set in the patient's ear, and use photoplethysmography (PPG) signals reflected by the skin of the ear to measure physiological information in the human body. In general, a PPG signal can be received by a light sensor that can receive green light, red light, and infrared light. The ear-hook oximeter uses the PPG signal to analyze and calculate data including heart rate, blood oxygen saturation, blood perfusion index (PI), etc.

However, if the user's ear structure is not easy to fit the ear-hook oximeter, or the signal light source does not touch the ear blood vessels, the quality of the PPG signal may be poor, and the physiological measurement data will be misjudged.

BRIEF SUMMARY OF THE DISCLOSURE

In order to resolve the issue described above, the present disclosure provides a method for calculating blood oxygen saturation. The method for calculating blood oxygen saturation includes defining the extreme value point of a non-red light signal as the extreme value point of a red light signal; and calculating the blood oxygen saturation according to the extreme value point of the red light signal.

According to the method disclosed above, the method further includes filtering the red light signal to eliminate outliers of the red light signal.

According to the method disclosed above, the method further includes obtaining a peak value when the red light signal has a first wave crest; obtaining a first valley value and a second valley value when the red light signal has two wave troughs adjacent to the first wave crest; calculating the average value of the first valley value and the second valley value; and calculating the difference between the peak value and the average value to obtain the AC value of the red light signal.

According to the method disclosed above, the step of filtering the red light signal includes eliminating the peak value, wherein the peak value is less than the first valley value or the second valley value.

According to the method disclosed above, the step of filtering the red light signal includes eliminating an intermediate value, wherein the intermediate value corresponds to the red light signal between the first wave crest and one of the two troughs adjacent to the first wave crest; wherein the intermediate value is larger than the peak value.

According to the method disclosed above, the step of filtering the red light signal includes eliminating the AC value, wherein the AC value corresponds to the AC value at the first wave crest and the AC value is more than 1.5 times the average AC value of the previous three wave crests in the red light signal earlier than the first wave crest.

According to the method disclosed above, the step of filtering the red light signal includes eliminating the AC value, wherein the AC value corresponds to the AC value at the first wave crest and the AC value is less than 0.67 times the average AC value of the previous three wave crests in the red light signal earlier than the first wave crest.

According to the method disclosed above, the method further includes obtaining the DC value of the red light signal according to the average value of the first valley value and the second valley value; and calculating the blood oxygen saturation according to the AC value and the DC value.

According to the method disclosed above, a time point when a wave crest of the non-red light signal occurs is a time point when a wave crest of a green light signal occurs; a time point when a wave trough of the non-red light signal occurs is a time point when a wave trough of an infrared light signal occurs; wherein the green light signal has dicrotic pulses, and the red light signal and the infrared light signal do not have dicrotic pulses.

According to the method disclosed above, the red light signal and the non-red light signal are photoplethysmography (PPG) signals.

The present disclosure also provides a computer programing product. The computer programing product is suitable for being loaded by an electronic device with a processor and executing a method for calculating blood oxygen saturation. The computer programing product includes a crest-to-trough alignment instruction, and a calculation instruction. The crest-to-trough alignment instruction allows the processor to define the extreme value point of a non-red light signal as the extreme value point of a red light signal. The calculation instruction allows the processor to calculate the blood oxygen saturation according to the extreme value point of the red light signal.

According to the computer programing product disclosed above, the computer programing product further includes a filtering instruction. The filtering instruction allows the processor to filter the red light signal to eliminate outliers of the red light signal.

According to the computer programing product disclosed above, the computer programing product further includes a wave crest alignment instruction, a trough alignment instruction, a wave trough average instruction, and an AC value calculation instruction. The wave crest alignment instruction allows the processor to obtain a peak value, wherein the red light signal has a first wave crest. The trough alignment instruction allows the processor to obtain a first valley value and a second valley value, wherein the red light signal has two wave troughs adjacent to the first wave crest. The trough average instruction allows the processor to calculate the average value of the first valley value and the second valley value. The AC value calculation instruction allows the processor to calculate the difference between the peak value and the average value to obtain the AC value of the red light signal.

The present disclosure also provides an electronic device. The electronic device includes a light emitting unit, a light sensor, and a processor. The light emitting unit is configured to emit a red light signal and a non-red light signal to a skin. The light sensor is configured to receive the red light signal and the non-red light signal reflected from the skin. The processor is configured to execute instructions and calculations, including defining the extreme value point of a non-red light signal as the extreme value point of a red light signal, and calculating the blood oxygen saturation according to the extreme value point of the red light signal.

According to the electronic device disclosed above, the processor is configured to execute further instructions and calculations, including: obtaining the peak value when the red light signal has a first wave crest; obtaining the first valley value and the second valley value when the red light signal has two wave troughs adjacent to the first wave crest; calculating the average value of the first valley value and the second valley value; and calculating the difference between the peak value and the average value to obtain the AC value of the red light signal.

BRIEF DESCRIPTION OF THE DRAWINGS

The disclosure can be more fully understood by reading the subsequent detailed description with references made to the accompanying figures. It should be understood that the figures are not drawn to scale in accordance with standard practice in the industry. In fact, it is allowed to arbitrarily enlarge or reduce the size of components for clear illustration. This means that many specific details, relationships and methods are disclosed to provide a complete understanding of the disclosure.

DETAILED DESCRIPTION OF THE DISCLOSURE

In order to make the above purposes, features, and advantages of some embodiments of the present disclosure more comprehensible, the following is a detailed description in conjunction with the accompanying drawings.

It should be understood that the words "comprise" and "include" used in the present disclosure are used to indicate the existence of specific technical features, values, method steps, operations, units and/or components. However, it does not exclude that more technical features, numerical values, method steps, work processes, units, components, or any combination of the above can be added.

The words "first" and "second" are used to describe components, they are not used to indicate the priority order of or advance relationship, but only to distinguish components with the same name.

The principle of photoplethysmography (PPG) is to pass through human tissue through a light source, and to receive continuous light signals from human tissue through a light sensor. When the light passes through human tissues, it is absorbed and attenuated by different human tissues. Therefore, the PPG signal is divided into two parts: direct current (DC) and alternating current (AC). Assuming that the composition of the human body is fixed, and the attenuation of light is also fixed, the DC value of the PPG signal is the absorbed part. The AC value of the PPG signal is a signal that is varied with changes of the volume of blood vessel.

Figure 1:
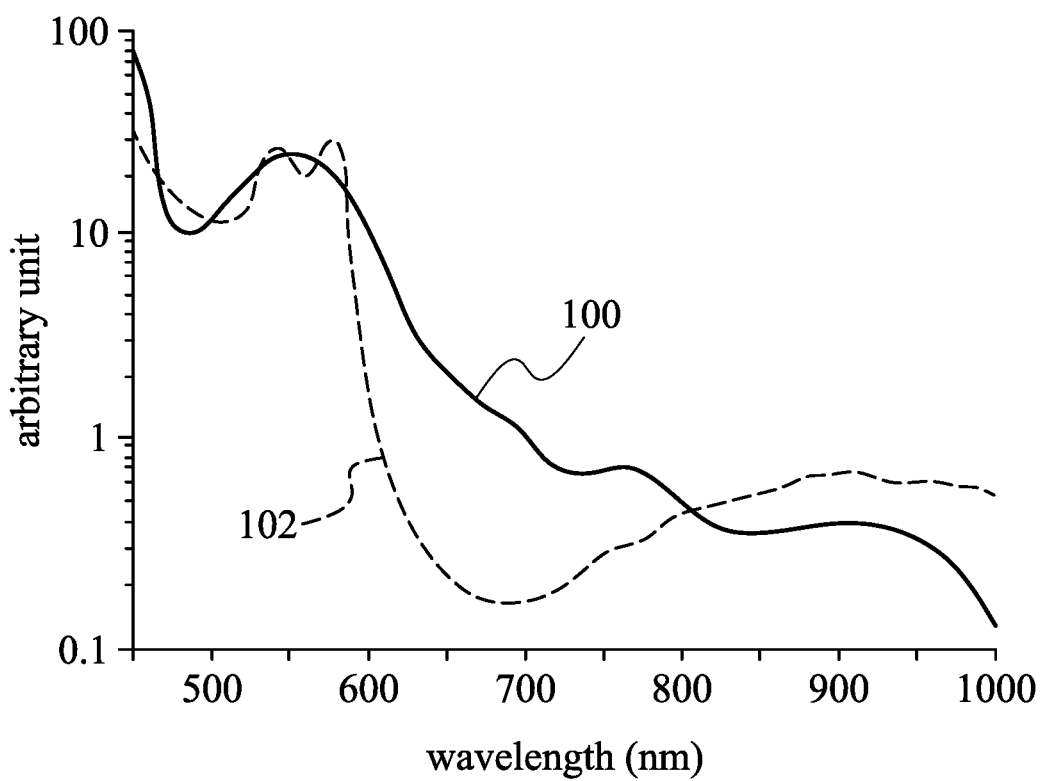
FIG. 1 is a schematic diagram of the absorption rate of oxyhemoglobin and hemoglobin in the blood to light of different wavelengths.

The PPG signal mainly has three light sources: green light, red light and infrared light. Different light sources have different penetration depths of human tissues. For example, the penetration depth of green light is the shallowest, the penetration depth of red light is second deepest, and the penetration depth of infrared is the deepest. FIG. 1 is a schematic diagram of an absorption rate of oxyhemoglobin and hemoglobin in the blood to light of different wavelengths. As shown in FIG. 1, curve 100 represents the absorption rate of hemoglobin in the blood to light of different wavelengths. Curve 102 represents the absorption rate of oxyhemoglobin in the blood to light of different wavelengths. Most of the green light with a wavelength of 530 nanometers is absorbed by red blood cells, so it can cause the attenuation of its light intensity and is suitable for calculating heart rate. Since hemoglobin and oxyhemoglobin have the most different absorption rate for red light with a wavelength of 660 nanometers and infrared light with a wavelength of 940 nanometers, for example, the absorption rate of hemoglobin to red light is higher than the absorption rate of oxyhemoglobin to red light, but the absorption rate of hemoglobin to infrared light is lower than the absorption rate of oxyhemoglobin to infrared light, red light and infrared light are suitable for calculating blood oxygen saturation.

Figure 2:
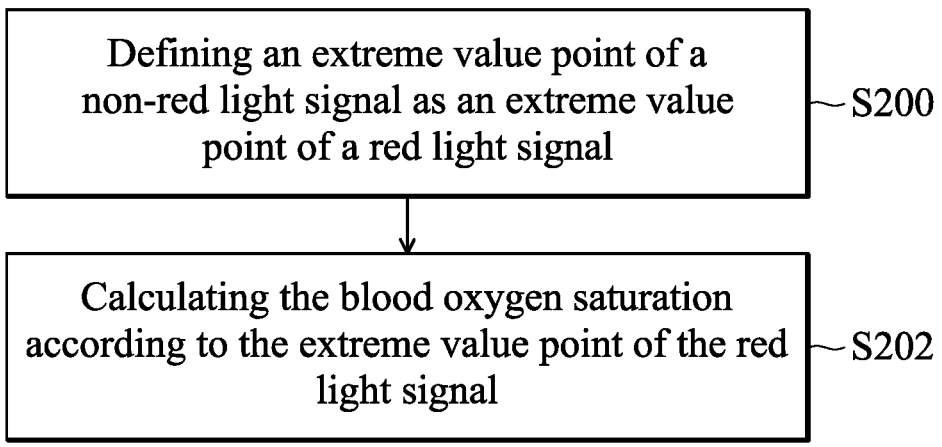
FIG. 2 is a flow chart of a method for calculating blood oxygen saturation in accordance with some embodiments of the disclosure.

FIG. 2 is a flow chart of a method for calculating blood oxygen saturation in accordance with some embodiments of the disclosure. As shown in FIG. 2, the method for calculating blood oxygen saturation of the embodiment of the disclosure first obtains a red light signal and a non-red light signal reflected from the skin. In some embodiments, the obtained red light signal and the obtained non-red light signal are reflected from the skin in the ear, but the present disclosure is not limited thereto. In step S200, the method for calculating blood oxygen saturation of the embodiment of the disclosure defines an extreme value point (for example, the wave crest or the wave trough) of the non-red light signal as an extreme value point of the red light signal. After that, in step S202, the method for calculating blood oxygen saturation of the embodiment of the disclosure calculates the blood oxygen saturation according to the extreme value point of the red light signal.

Figure 3:
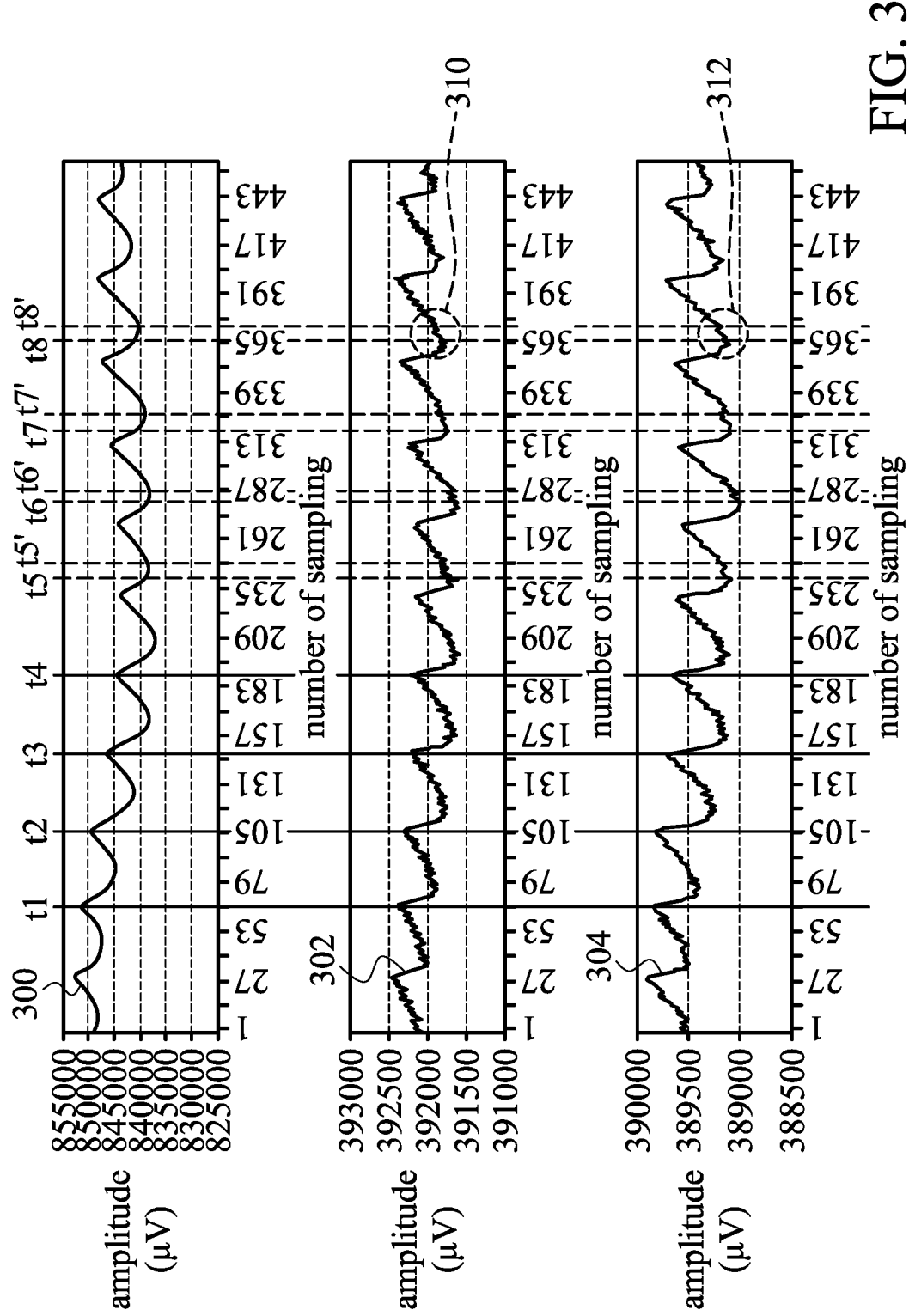
FIG. 3 is a waveform diagram of green light signal 300, red light signal 302, and infrared light signal 304 in accordance with some embodiments of the disclosure.

In some embodiments, the non-red light signal is a green light signal and/or an infrared light signal. In some embodiments, the red light signal and the non-red light signal are emitted by a light emitting unit of an ear-hook electronic device. For example, the light emitting unit of the ear-hook electronic device includes a green LED, a red LED, and an infrared LED to respectively emit corresponding green light signals, red light signals and infrared light signals. FIG. 3 is a waveform diagram of green light signal 300, red light signal 302, and infrared light signal 304 in accordance with some embodiments of the disclosure. In some embodiments of FIG. 3, the horizontal axis is the number of samples, and the vertical axis is the amplitude (μV), wherein the number of samples can correspond to time. In some embodiments, the waveform diagram in FIG. 3 is read from a light sensor of an ear-hook electronic device. The light sensor is used to receive the green light signal 300, the red light signal 302, and the infrared light signal 304 reflected from the skin.

As shown in FIG. 3, the green light signal 300, the red light signal 302, and the infrared light signal 304 all have peaks at time point t1, time point t2, time point t3, and time point t4. In other words, since the wave crest of the green light signal 300, the wave crest of the red light signal 302, and the wave crest of the infrared light signal 304 are aligned with each other at the time point t1, the time point t2, the time point t3, and the time point t4, the method for calculating the blood oxygen saturation in the embodiment of the present disclosure can use a time point when the green light signal 300 or the infrared light signal 304 has a wave crest, as a time point when the red light signal 302 has a wave crest. After that, the red light signal 302 and the infrared light signal 304 have wave troughs at time point t5, time point t6, time point t7, and the time point t8, but the green light 300 does not have wave troughs until time point t5', time point t6', time point t7', and time point t8'. In other words, the wave trough of the red light signal 302 is aligned with the wave trough of the infrared light signal 304 at the time points t5, t6, t7, and d8, but the wave trough of the red light signal 302 is not aligned with the wave trough of the green light signal 300 at the time points t5, t6, t7, and d8.

In some embodiments, since the red light signal 302 and the infrared light signal 304 have dicrotic pulses of the physiological characteristic from the human body from the time points t5 to t5', time points t6 to t6', time points t7 to t7' and time points t8 to t8' (for example, dicrotic pulses 310 and 312 at time point t8 to t8'), the wave trough of the red light signal 302 and the wave trough of the infrared light signal 304 cannot be aligned with the wave trough of the green light signal 300. In some embodiments, the dicrotic pulses come from the reflected shock wave formed by the blood hitting the aortic valve caused by the aortic blood pressure. Therefore, the method for calculating the blood oxygen saturation of the present disclosure uses the time point (for example, time points t1-t4) when the non-red light signal (for example, the green light signal 300 or the infrared light signal 304) has a wave crest, as the time point when the red light signal 302 has a wave crest. Furthermore, the method for calculating the blood oxygen saturation of the embodiment of the disclosure uses the time point (for example, time points t5-t8) when the non-red light signal (for example, the infrared light 304) has a wave trough, as the time point when the red light signal 302 has a wave trough.

In some embodiments, the green light signal 300 has a short wavelength and a shallow penetration depth, so the green light signal 300 may be directly absorbed by blood vessels. In other words, since human tissue has a good absorption rate of the green light signal 300, the changes in blood flow that can be reflected by the green light signal 300 are more obvious, the amplitude of the green light signal 300 becomes larger (for example, the amplitude of the green light signal 300 in FIG. 3 is greater than that of the red light signal 302 and the infrared light signal 304), and the interference may be smaller (that is, the higher signal-to-noise ratio (SNR)). The red light signal 302 and infrared light signal 304 have longer wavelengths, and their penetration depths are deeper than the penetration depth of the green light signal 300, making them easier to hit bones and other human tissues. Thus, the red light signal 302 and the infrared light signal 304 may be more sensitive and more susceptible to interference. Therefore, the method for calculating the blood oxygen saturation of the embodiment of the disclosure uses the time point when the green light signal 300 has a wave crest, as the time point when the red light signal 302 has a wave crest.

In some embodiments, the light emitting unit of the ear-hook electronic device does not emit three light sources (such as the green light signal 300, the red light signal 302, and the infrared light signal 304) at the same time, but emits three light sources one by one according to the design of the firmware. However, since the switching time for the light emitting unit of the ear-hook electronic device to switch out the three light sources is very short (that is, the light source switching speed is very fast), the method for calculating the blood oxygen saturation in the embodiment of the present disclosure can achieve the waveform alignment method of step S200. The method for calculating the blood oxygen saturation in the embodiment of the disclosure first retrieves an extreme value of the PPG signal (for example, the green light signal 300, the red light signal 302, and the infrared light signal 304) to calculate the physiological measurement. For example, the wave crest of the green light signal 300 is used to calculate the heart rate, the wave crest and wave trough of the infrared light signal 304 are used to calculate the blood perfusion index, and the wave crest and wave trough of the red light signal 302 and the infrared light signal 304 are used to calculate the blood oxygen saturation.

Table 1 is a statistical table of embodiments of the method for calculating the blood oxygen saturation of the present disclosure using the time point of the wave crest or wave trough of auxiliary signals (for example, the green light signal 300 and the infrared light signal 304 in FIG. 1) as the time point of the wave crest or wave trough of the red light signal 302 in FIG. 1.

TABLE 1

| | Auxiliary signals selection | | | | | | |
| --- | --- | --- | --- | --- | --- | --- | --- |
| | Wave crest | | | Wave trough | | | Calculation |
| Extreme value Absorption rate | Good (green light) | Worse (red light) | Middle (infrared light) | Good (green light) | Worse (red light) | Middle (infrared light) | result of blood oxygen saturation |
| embodiments 1 | ✓ | | | ✓ | | | 91% |
| 2 | ✓ | | | | ✓ | | 95% |
| 3 | ✓ | | | | | ✓ | 98% |
| 4 | | ✓ | | ✓ | | | 88% |
| 5 | | ✓ | | | ✓ | | 95% |
| 6 | | ✓ | | | | ✓ | 96% |

TABLE 1-continued

| | Auxiliary signals selection | | | | | | Calculation |
| --- | --- | --- | --- | --- | --- | --- | --- |
| | Wave crest | | | Wave trough | | | |
| Extreme value Absorption rate | Good (green light) | Worse (red light) | Middle (infrared light) | Good (green light) | Worse (red light) | Middle (infrared light) | result of blood oxygen saturation |
| 7 | | | ✓ | ✓ | | | 89% |
| 8 | | | ✓ | | ✓ | | 93% |
| 9 | | | ✓ | | | ✓ | 99% |

Remarks:
The blood oxygen saturation is calculated by averaging the data from measurement device for wearing 30 seconds.

The reference standard for the blood oxygen saturation in Table 1 is a fingertip pulse oximeter, which is a medical product. As shown in Table 1, in an embodiment 1, the method for calculating the blood oxygen saturation of the present disclosure defines the time point when the green light signal 300 has a wave crest, as the time point when the red light signal 302 has a wave crest in step S200, and defines the time point when the green light signal 300 has a wave trough, as the time point when the red light signal 302 has a wave trough in step 200. According to FIG. 3, since the wave trough of the green light signal 300 is not aligned with the wave trough of the red light signal 302, the accuracy rate of the blood oxygen saturation calculated in step S202 of the method for calculating the blood oxygen saturation of the present disclosure is 91%. In an embodiment 2, the method for calculating the blood oxygen saturation of the present disclosure defines the time point when the green light signal 300 has a wave crest, as the time point when the red light signal 302 has a wave crest in step S200, but any time point of auxiliary signals is not used as the time point when the red light signal 302 has a wave trough, that is, the time point when the red light signal 302 has the wave trough is directly used. Therefore, the accuracy rate of the blood oxygen saturation calculated in step S202 of the method for calculating the blood oxygen saturation of the present disclosure is 95%.

In an embodiment 3, the method for calculating the blood oxygen saturation of the present disclosure defines the time point when the green light signal 300 has a wave crest, as the time point when the red light signal 302 has a wave crest in step S200, and defines the time point when the infrared light signal 304 has a wave trough, as the time point when the red light signal 302 has a wave trough in step 200. Therefore, the accuracy rate of the blood oxygen saturation calculated in step S202 of the method for calculating the blood oxygen saturation of the present disclosure is 98%. In an embodiment 4, the method for calculating the blood oxygen saturation of the present disclosure does not define any time point of auxiliary signals, as the time point when the red light signal 302 has a wave crest, and defines the time point when the green light signal 300 has a wave trough, as the time point when the red light signal 302 has a wave trough. According to FIG. 3, since the wave trough of the green light signal 300 is not aligned with the wave trough of the red light signal 302, the accuracy rate of the blood oxygen saturation calculated in step S202 of the method for calculating the blood oxygen saturation of the present disclosure is 88%.

In an embodiment 5, the method for calculating the blood oxygen saturation of the present disclosure does not define any time point of auxiliary signals, as the time point when the red light signal 302 has a wave crest, and also does not use any time point of auxiliary signals, as the time point when the red light signal 302 has a wave trough. In other words, the method for calculating the blood oxygen saturation of the present disclosure directly calculates the blood oxygen saturation according to the wave crest and the wave trough of the red light signal 302, and the accuracy rate of the calculated blood oxygen saturation is 95%. In an embodiment 6, the method for calculating the blood oxygen saturation of the present disclosure does not define any time point of auxiliary signals, as the time point when the red light signal 302 has a wave crest, and defines the time point when the infrared light signal 304 has a wave trough, as the time point when the red light signal 302 has a wave trough in step 200. According to FIG. 3, since the wave trough of the infrared light signal 304 is aligned with the wave trough of the red light signal 302, the accuracy rate of the blood oxygen saturation calculated in step S202 of the method for calculating the blood oxygen saturation of the present disclosure is 95%.

In an embodiment 7, the method for calculating the blood oxygen saturation of the present disclosure defines the time point when the infrared light signal 304 has a wave crest, as the time point when the red light signal 302 has a wave crest in step S200, and defines the time point when the green light signal 300 has a wave trough, as the time point when the red light signal 302 has a wave trough in step S200. According to FIG. 3, since the wave trough of the green light signal 300 is not aligned with the wave trough of the red light signal 302, the accuracy rate of the blood oxygen saturation calculated in step S202 of the method for calculating the blood oxygen saturation of the present disclosure is 89%. In an embodiment 8, the method for calculating the blood oxygen saturation of the present disclosure defines the time point when the infrared light signal 304 has a wave crest, as the time point when the red light signal 302 has a wave crest in step S200, but does not define any time point of auxiliary signals, as the time point when the red light signal 302 has a wave trough, that is, the time point when the red light signal 302 has the wave trough is directly used. Therefore, the accuracy rate of the blood oxygen saturation calculated in step S202 of the method for calculating the blood oxygen saturation of the present disclosure is 93%.

In an embodiment 9, the method for calculating the blood oxygen saturation of the present disclosure defines the time point when the infrared light signal 304 has a wave crest, as the time point when the red light signal 302 has a wave crest in step S200, and defines the time point when the infrared light signal 304 has a wave trough, as the time point when the red light signal 302 has a wave trough in step S200. According to FIG. 3, since the wave crest and the wave trough of the infrared light signal 304 are all aligned with the wave crest and the wave trough of the red light signal 302, the accuracy rate of the blood oxygen saturation calculated in step S202 of the method for calculating the blood oxygen saturation of the present disclosure is 99%. According to the embodiments 1-9, the method for calculating the blood oxygen saturation of the present disclosure can use a light source with a better absorption rate (for example, the green light signal 300 and/or the infrared light signal 304) to assist a light source with a poor absorption rate (for example, the red light signal 302).

Figure 4:
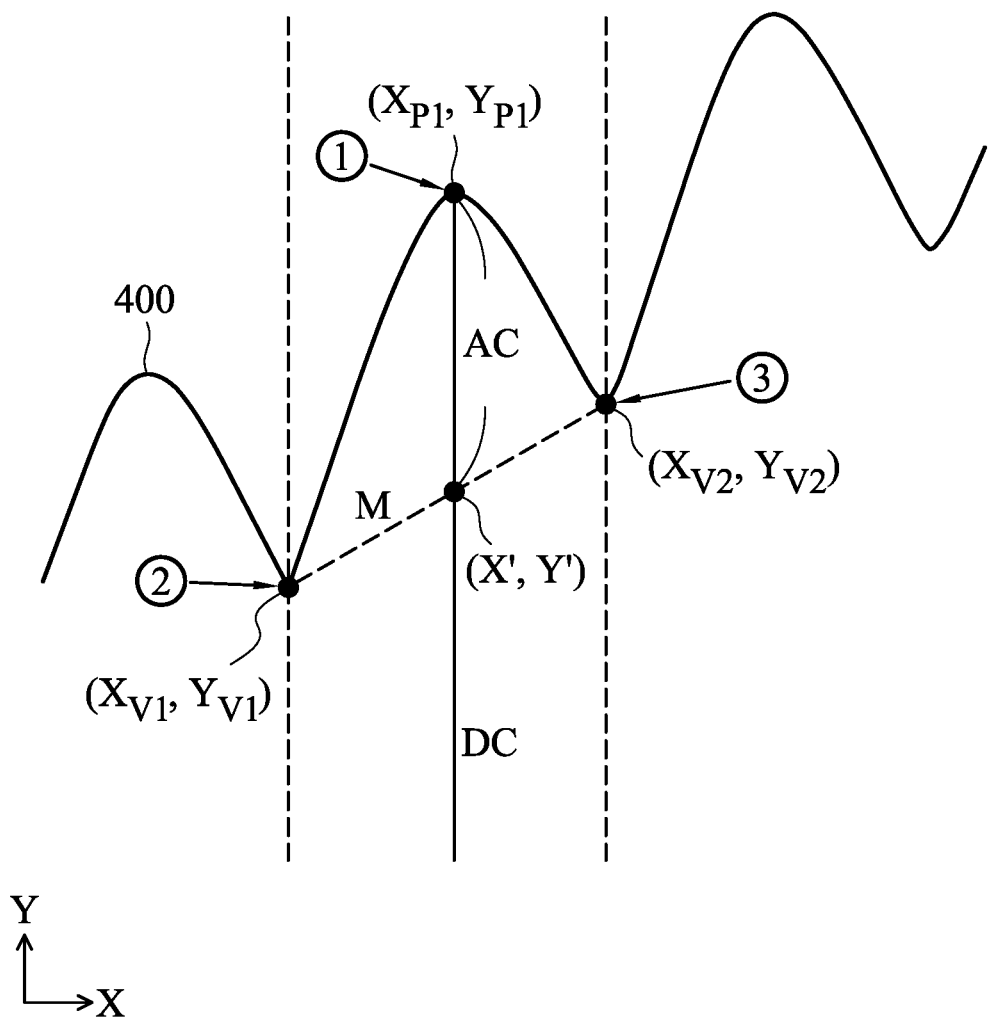
FIG. 4 is a schematic diagram of calculating the AC value and DC value of a PPG signal 400 in accordance with some embodiments of the disclosure.

FIG. 4 is a schematic diagram of calculating the AC value and DC value of a PPG signal 400 in accordance with some embodiments of the disclosure. As shown in FIG. 4, in order to obtain the AC value and the DC value of the PPG signal 400 (for example, the green light signal 300, the red light signal 302, and the infrared light signal 304 in FIG. 1), the method for calculating the blood oxygen saturation of the present disclosure first obtains a peak value ($X_{P1}$, $Y_{P1}$) of the PPG signal 400 at a wave crest ①. Then, the method for calculating the blood oxygen saturation of the present disclosure obtains a valley value ($X_{V1}$, $Y_{V1}$) of the PPG signal 400 at a wave trough ② and a valley value ($X_{V2}$, $Y_{V2}$) of the PPG signal 400 at a wave trough ③. After that, the method for calculating the blood oxygen saturation of the present disclosure calculates the average value (X', Y') of the valley value ($X_{V1}$, $Y_{V1}$) of the PPG signal 400 at the wave trough ② and the valley value ($X_{V2}$, $Y_{V2}$) of the PPG signal 400 at the wave trough ③. In some embodiments, the method for calculating the blood oxygen saturation of the present disclosure uses equation 1 to calculate a slope M from the valley value ($X_{V1}$, $Y_{V1}$) to the valley value ($X_{V2}$, $Y_{V2}$).

$$M = \frac{Y_{V2} - Y_{V1}}{X_{V2} - X_{V1}} \qquad \text{equation 1}$$

Referring to FIG. 4, since X'=$X_{P1}$, Y' can be obtained through the slope M. Finally, the method for calculating the blood oxygen saturation of the present disclosure calculates the difference between the peak value ($X_{P1}$, $Y_{P1}$) and the average value (X', Y') to obtain the AC value of the PPG signal 400, for example, the AC value is equal to $Y_{P1}$−Y'. Then, the method for calculating the blood oxygen saturation of the present disclosure calculates the difference between the average value (X', Y') and the X axis (that is y=0) to obtain a DC value of the PPG signal 400, for example, the DC value is equal to Y'.

In some embodiments, the method for calculating the blood oxygen saturation of the present disclosure uses equation 2 to calculate the blood oxygen saturation (SpO2).

$$\text{blood oxygen saturation } (SpO2) = 115 - 25 \times \frac{\frac{R_{ac}}{R_{dc}}}{\frac{IR_{ac}}{IR_{dc}}} \qquad \text{equation 2}$$

In equation 2, $R_{ac}$ is the AC value of the red light signal 302, $R_{dc}$ is the DC value of the red light signal 302, $IR_{ac}$ is the AC value of the infrared light signal 304, and $IR_{dc}$ is the DC value of the infrared light signal 304.

In some embodiments, the method for calculating the blood oxygen saturation of the present disclosure uses equation 3 to calculate blood perfusion index. The blood perfusion index is an index used to observe blood flow.

$$\text{blood perfusion index} = \frac{IR_{ac}}{IR_{dc}} \qquad \text{equation 3}$$

In equation 3, $IR_{ac}$ is the AC value of the infrared light signal 304, and $IR_{dc}$ is the DC value of the infrared light signal 304.

Figure 5A:
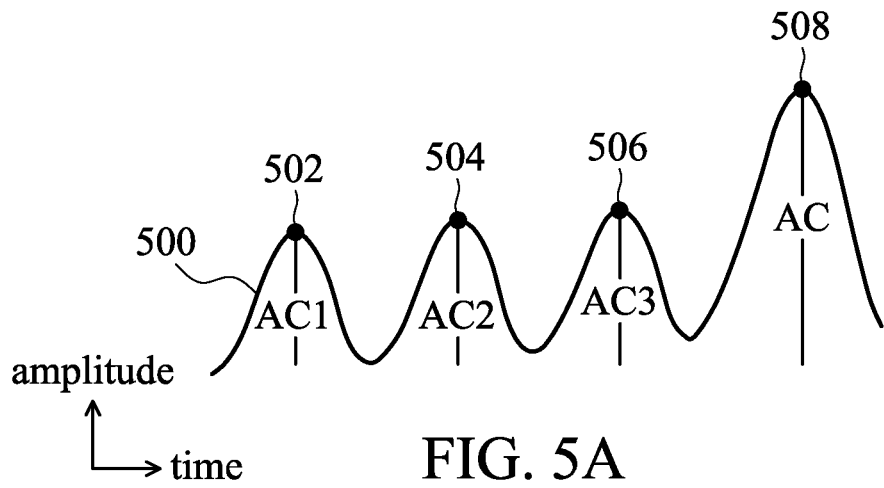
FIG. 5A is a schematic diagram of a scene 1 of filtering a PPG signal 500 in accordance with some embodiments of the disclosure.

After step S200 is completed and before step S202 is performed, the method for calculating the blood oxygen saturation of the present disclosure further filters the red light signal 302 to eliminate outliers of the red light signal 302. FIG. 5A is a schematic diagram of a scene 1 of filtering a PPG signal 500 in accordance with some embodiments of the disclosure. As shown in FIG. 5A, the PPG signal 500 (for example, the red light signal 302) in the embodiment of the present disclosure has a wave crest 502, a wave crest 504, a wave crest 506, and a wave crest 508. At the wave crest 502, the PPG signal 500 has an AC value (AC1). At the wave crest 504, the PPG signal 500 has an AC value (AC2). At the wave crest 506, the PPG signal 500 has an AC value (AC3). At the wave crest 508, the PPG signal 500 has an AC value (AC). When the AC value (AC) of the PPG signal 500 at the wave crest 508 is more than 1.5 times the average value (for example, the average value is equal to (AC1+AC2+AC3)/3) of the AC value (AC1) at the wave crest 502, the AC value (AC2) at the wave crest 504, and the AC value (AC3) at the wave crest 506, the method for calculating the blood oxygen saturation of the present disclosure eliminates the AC value (AC) at the wave crest 508. In other words, the method for calculating the blood oxygen saturation of the present disclosure does not use the AC value (AC) at the wave crest 508 as the basis for calculating the blood oxygen saturation in step S202.

Figure 5B:
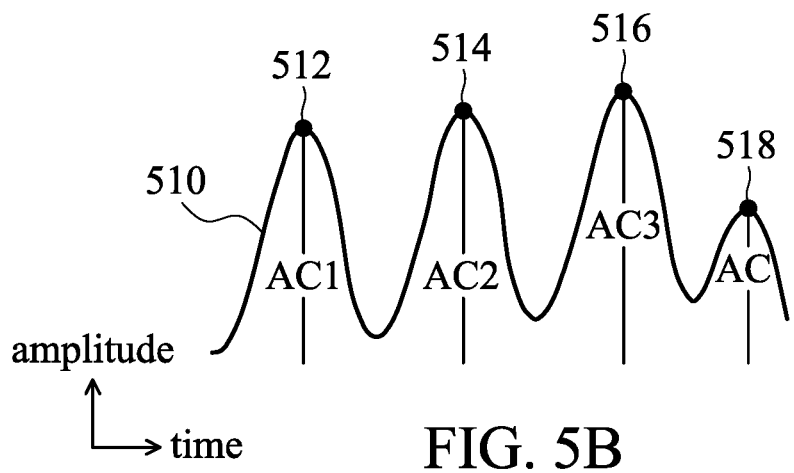
FIG. 5B is a schematic diagram of a scene 2 of filtering a PPG signal 510 in accordance with some embodiments of the disclosure.

FIG. 5B is a schematic diagram of a scene 2 of filtering a PPG signal 510 in accordance with some embodiments of the disclosure. As shown in FIG. 5B, the PPG signal 500 (for example, the red light signal 302) in the embodiment of the present disclosure has a wave crest 512, a wave crest 514, a wave crest 516, and a wave crest 518. At the wave crest 512, the PPG signal 500 has an AC value (AC1). At the wave crest 514, the PPG signal 500 has an AC value (AC2). At the wave crest 516, the PPG signal 500 has an AC value (AC3). At the wave crest 518, the PPG signal 500 has an AC value (AC). When the AC value (AC) of the PPG signal 500 at the wave crest 518 is less than 0.67 times the average value (for example, the average value is equal to (AC1+AC2+AC3)/3) of the AC value (AC1) at the wave crest 512, the AC value (AC2) at the wave crest 514, and the AC value (AC3) at the wave crest 516, the method for calculating the blood oxygen saturation of the present disclosure eliminates the AC value (AC) at the wave crest 518. In other words, the method for calculating the blood oxygen saturation of the present disclosure does not use the AC value (AC) at the wave crest 518 as the basis for calculating the blood oxygen saturation in step S202.

Figure 5C:
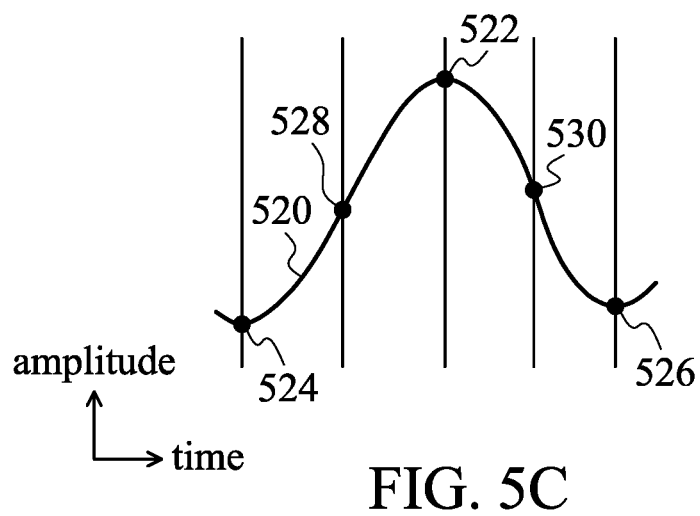
FIG. 5C is a schematic diagram of a scene 3 of filtering a PPG signal 520 in accordance with some embodiments of the disclosure.

FIG. 5C is a schematic diagram of a scene 3 of filtering a PPG signal 520 in accordance with some embodiments of the disclosure. As shown in FIG. 5C, the PPG signal 520 (for example, the red light signal 302) in the embodiment of the present disclosure has a wave crest 522, a wave trough 524, and a wave trough 526. When the AC value of the PPG signal 520 at a point 528 between the wave crest 522 and the wave trough 524 is greater than the AC value of the PPG signal 520 at the wave crest 522 (that is, the peak value), or the AC value of the PPG signal 520 at a point 530 between the wave crest 522 and the wave trough 526 is greater than the AC value of the PPG signal 520 at the wave crest 522, the method for calculating the blood oxygen saturation of the present disclosure eliminates the AC value at the point 528 or the point 530 in the PPG signal 520. In other words, the method for calculating the blood oxygen saturation of the present disclosure does not use the AC value at the point 528 or the point 530 as the basis for calculating the blood oxygen saturation in step S202.

In some embodiments, as shown in FIG. 5C, when the AC value at the wave crest 522 (that is, the peak value) is less than or equal to the AC value at the wave trough 524 or the AC value at the wave trough 526, the AC value at the wave crest 522 is eliminated. In other words, the method for calculating the blood oxygen saturation of the present disclosure does not use the AC value at the wave crest 522 as the basis for calculating the blood oxygen saturation in step S202.

The embodiment of the present disclosure also discloses a computer programming product suitable for an electronic device with a processor. In some embodiments, the electronic device executes a crest-to-trough alignment instruction, and a calculation instruction. The crest-to-trough alignment instruction enables the processor to execute step S200 in FIG. 2. The calculation instruction enables the processor to execute step S202 in FIG. 2. After the execution of the crest-to-trough alignment instruction is completed, and before the calculation instruction is executed, the electronic device of the embodiment of the present disclosure further executes a filtering instruction. The filtering instruction enables the processor to filter the red light signal 302 in the manner of scene 1 in FIG. 5A, scene 2 in FIG. 5B and scene 3 in FIG. 5C, so as to eliminate outliers of the red light signal 302.

In some embodiments, the electronic device of the embodiment of the disclosure further executers a wave crest alignment instruction, a wave trough alignment instruction, a wave trough average instruction, and an AC value calculation instruction. The wave crest alignment instruction enables the processor to obtain a peak value when the red light signal has a first wave crest (for example, the peak value $(X_{P1}, Y_{P1})$ of the PPG signal 400 at the wave crest ① in FIG. 4). The wave trough alignment instruction enables the processor to obtain a first valley value and a second valley value when the red light signal has two wave troughs adjacent to the first wave crest (for example, the valley value $(X_{V1}, Y_{V1})$ of the PPG signal 400 at the wave trough ② and the valley value $(X_{V2}, Y_{V2})$ of the PPG signal 400 at the wave trough ③ in FIG. 4). The wave trough average instruction enables the processor to calculate the average value of the first valley value and the second valley value (for example, calculating the average value (X', Y') of the valley value $(X_{V1}, Y_{V1})$ of the PPG signal 400 at the wave trough ② and the valley value $(X_{V2}, Y_{V2})$ of the PPG signal 400 at the wave trough ③ in FIG. 4). The AC value calculation instruction enables the processor to calculate the difference between the peak value and the average value to obtain the AC value of the red light signal (for example, calculating the difference between the peak value $(X_{P1}, Y_{P1})$ and the average value (X', Y') to obtain the AC value of the PPG signal 400 in FIG. 4).

Figure 6:
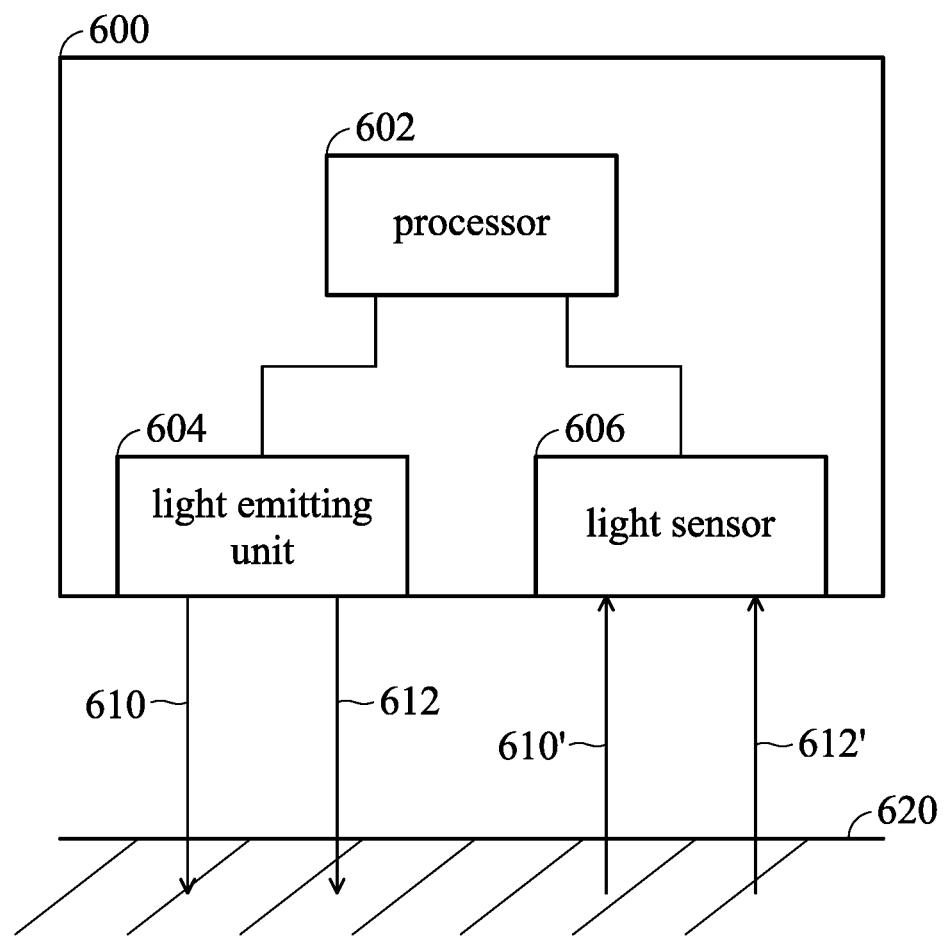
FIG. 6 is a block diagram of an electronic device in accordance with some embodiments of the disclosure.

The embodiment of the present disclosure also discloses an electronic device. FIG. 6 is a block diagram of an electronic device 600 in accordance with some embodiments of the disclosure. In some embodiments, the electronic device 600 is an ear-hook electronic device. The electronic device 600 includes a light emitting unit 604, a light sensor 606, and a processor 602. The light emitting unit 604 is configured to emit a red light signal 610 and at least one non-red light signal 612 to a skin 620. In some embodiments, the light emitting unit 604 includes a green LED, a red LED, and an infrared LED (not shown), but the present disclosure is not limited thereto. The light sensor 606 is configured to receive the red light signal 610' (for example, the red light signal 302) and the at least one non-red light signal 612' (for example, the green light signal 300 and/or the infrared light signal 304) reflected from the skin 620. In some embodiments, the light sensor 606 transmits the received light signals to the processor 602 in digital form. Then, the processor 602 executes steps S200 and S202 in FIG. 2. In some embodiments, after the processor 602 completes step S200 and before step S202, the processor 602 further filters the reflected red light signal 610' in the manner of scene 1 in FIG. 5A, scene 2 in FIG. 5B, and scene 3 in FIG. 5C to eliminate outliers of the reflected red light signal 610'.

In some embodiments, the processor 602 executes further tasks including: obtaining a peak value when the red light signal 610' has a first wave crest (for example, the peak value $(X_{P1}, Y_{P1})$ of the PPG signal 400 at the wave crest ① in FIG. 4); obtaining a first valley value and a second valley value when the red light signal 610' has two wave troughs adjacent to the first wave crest (for example, the valley value $(X_{V1}, Y_{V1})$ of the PPG signal 400 at the wave trough ② and the valley value $(X_{V2}, Y_{V2})$ of the PPG signal 400 at the wave trough ③ in FIG. 4); calculating the average value of the first valley value and the second valley value (for example, calculating the average value (X', Y') of the valley value $(X_{V1}, Y_{V1})$ of the PPG signal 400 at the wave trough ② and the valley value $(X_{V2}, Y_{V2})$ of the PPG signal 400 at the wave trough ③ in FIG. 4); and calculating the difference between the peak value and the average value to obtain the AC value of the red light signal 610' (for example, calculating the difference between the peak value $(X_{P1}, Y_{P1})$ and the average value (X', Y') to obtain the AC value of the PPG signal 400 in FIG. 4).

In some embodiments, before executing step S200, the processor 602 of the electronic device 600 of the present disclosure further executes a wearing stability judgment to detect whether the user is in a static state. If the user is not in the static state (for example, the user's movement is too large), the processor 602 may not perform step S200. In some embodiments, the processor 602 of the electronic device 600 of the present disclosure executes a dynamic timing warping (DTW). In short, the processor 602 first receives a template waveform from the PPG signal, and uses the template waveform as a reference. After that, when the processor 602 receives the subsequent PPG signal from the light sensor 606, the processor 602 may match the waveform of each subsequent PPG signal with the template waveform to determine whether each PPG signal is a good signal.

The embodiments of the present disclosure are disclosed above, but they are not used to limit the scope of the present disclosure. A person skilled in the art can make some changes and retouches without departing from the spirit and scope of the embodiments of the present disclosure. Therefore, the scope of protection in the present disclosure shall be deemed as defined by the scope of the attached claims.

What is claimed is:
1. A method for calculating blood oxygen saturation, comprising:
    detecting a green light signal, an infrared light signal, and a red light signal from a skin;

assigning an extreme value point of the green light signal and the infrared light signal to an extreme value point of a red light signal to obtain a period of the red light signal; and calculating the blood oxygen saturation according to the extreme value point in the period of the red light signal;

wherein a time point when the green light signal or the infrared light signal has a wave crest is a time point when the red light signal has a wave crest; and wherein a time point when the infrared light has a wave trough is a time point when the red light signal has a wave trough; and wherein the green light signal has dicrotic pulse, and the red light signal and the infrared light signal do not have dicrotic pulse.

2. The method as claimed in claim 1, further comprising:
filtering the red light signal to eliminate outliers of the red light signal.

3. The method as claimed in claim 2, further comprising:
obtaining a peak value when the red light signal has a first wave crest;
obtaining a first valley value and a second valley value when the red light signal has two troughs adjacent to the first wave crest;
calculating an average value of the first valley value and the second valley value; and
calculating a difference between the peak value and the average value to obtain an alternating current (AC) value of the red light signal.

4. The method as claimed in claim 3, wherein the step of filtering the red light signal comprises:
eliminating the peak value, wherein the peak value is lower than the first valley value or the second valley value.

5. The method as claimed in claim 3, wherein the step of filtering the red light signal comprises:
eliminating an intermediate value, wherein the intermediate value corresponds to the red light signal between the first wave crest and one of the two troughs adjacent to the first wave crest; and the intermediate value is higher than the peak value.

6. The method as claimed in claim 3, wherein the step of filtering the red light signal comprises:
eliminating the AC value, wherein the AC value corresponds to the AC value at the first wave crest and the AC value is more than 1.5 times an average AC value of the previous three wave crests in the red light signal earlier than the first wave crest.

7. The method as claimed in claim 3, wherein the step of filtering the red light signal comprises:
eliminating the AC value, wherein the AC value corresponds to the AC value at the first wave crest and the AC value is less than 0.67 times the average AC value of the previous three wave crests in the red light signal earlier than the first wave crest.

8. The method as claimed in claim 3, further comprising:
obtaining a direct current (DC) value of the red light signal according to the average value of the first valley value and the second valley value; and
calculating the blood oxygen saturation according to the AC value and the DC value.

9. The method as claimed in claim 2, wherein the red light signal, the green light signal, and the infrared light signal are photoplethysmography (PPG) signals.

10. An electronic device, comprising:
a light emitting unit, configured to emit a red light signal, a green light signal, and an infrared light signal to a skin;
a light sensor, configured to receive the red light signal, the green light signal, and the infrared light signal reflected from the skin; and
a processor, configured to execute comprising:
assigning the extreme value point of the green light signal and the infrared light signal to the extreme value point of the red light signal to obtain a period of the red light signal; and
calculating the blood oxygen saturation according to the extreme value point in the period of the red light signal;
wherein a time point when the green light signal or the infrared light signal has a wave crest is a time point when the red light signal has a wave crest; and
wherein a time point when the infrared light has a wave trough is a time point when the red light signal has a wave trough; and
wherein the green light signal has dicrotic pulse, and the red light signal and the infrared light signal do not have dicrotic pulse.

11. The electronic device as claimed in claim 10, wherein the processor is configured to execute further comprising:
filtering the red light signal to eliminate outliers of the red light signal.

12. The electronic device as claimed in claim 10, wherein the processor is configured to execute further comprising:
obtaining a peak value when the red light signal has a wave crest;
obtaining a first valley value and a second valley value when the red light signal has two wave troughs adjacent to the first wave crest;
calculating the average value of the first valley value and the second valley value; and
calculating the difference between the peak value and the average value to obtain the AC value of the red light signal.

* * * * *